(12) United States Patent
Watanabe et al.

(10) Patent No.: US 10,512,434 B2
(45) Date of Patent: Dec. 24, 2019

(54) BRAIN ACTIVITY MEASUREMENT DEVICE, PROGRAM, AND METHOD

(71) Applicant: NIPRO CORPORATION, Osaka (JP)

(72) Inventors: Yuri Watanabe, Machida (JP); Yohei Kobayashi, Machida (JP); Toshimitsu Musha, Machida (JP); Yukio Kosugi, Tokyo (JP); Takashi Asada, Moriya (JP)

(73) Assignee: NIPRO CORPORATION, Osaka (JP)

( * ) Notice: Subject to any disclaimer, the term of this patent is extended or adjusted under 35 U.S.C. 154(b) by 384 days.

(21) Appl. No.: 15/327,500

(22) PCT Filed: Jul. 22, 2015

(86) PCT No.: PCT/JP2015/070893
§ 371 (c)(1),
(2) Date: Apr. 27, 2017

(87) PCT Pub. No.: WO2016/013596
PCT Pub. Date: Jan. 28, 2016

(65) Prior Publication Data
US 2017/0245804 A1      Aug. 31, 2017

(30) Foreign Application Priority Data

Jul. 22, 2014  (JP) ................... 2014-149205
Sep. 26, 2014  (JP) ................... 2014-197420

(51) Int. Cl.
*A61B 5/00*      (2006.01)
*A61B 5/0476*    (2006.01)
(Continued)

(52) U.S. Cl.
CPC .......... *A61B 5/7246* (2013.01); *A61B 5/0476* (2013.01); *A61B 5/4088* (2013.01);
(Continued)

(58) Field of Classification Search
None
See application file for complete search history.

(56) References Cited

U.S. PATENT DOCUMENTS

| 2014/0107464 A1* | 4/2014 | Aksenova | A61B 5/04009 600/409 |
| 2014/0121724 A1* | 5/2014 | Chichilnisky | A61N 1/36046 607/54 |

(Continued)

FOREIGN PATENT DOCUMENTS

JP          5118230 B2      1/2013

OTHER PUBLICATIONS

Bin He et al.; Electric Dipole Tracing in the Brain by Means of the Boundary Element Method and Its Accuracy; IEEE Transactions on Biomedical Engineering; vol. BME-34; No. 6; Jun. 1987; pp. 406-414.

(Continued)

*Primary Examiner* — Etsub D Berhanu
(74) *Attorney, Agent, or Firm* — Studebaker & Brackett PC

(57) ABSTRACT

It is intended to quantitatively evaluate deterioration in brain function associated with a disease such as dementia, with a high degree of accuracy by a simplified method using signals acquired from a few sensors arranged on the scalp. The present invention relates to a brain activity measurement device comprising: a signal acquisition part configured to acquire a signal from a brain of the subject, using three sensors attached to different locations on the surface of the head of a subject; a data extraction part configured to extract, from each of the three signals acquired from respective ones of the sensors, a deep-brain potential signal having a specific frequency band arising from an activity of a deep brain region, and acquire data from the extracted deep-brain potential signal with a sampling period; a correlation value (Continued)

calculation part configured to calculate a correlation value indicative of a correlative relationship among the deep-brain potential signals acquired from each respective sensors, based on a phase relationship among three pieces of time-series data each extracted from the respective sensors by the data extraction part; and an index value calculation part configured to analyze the deep-brain potential signals from the deep brain region, based on the calculated correlation value, to calculate an index value for determining a brain function.

10 Claims, 15 Drawing Sheets

(51) Int. Cl.
    *G16H 50/30* (2018.01)
    *G16H 40/63* (2018.01)
    *G16H 50/50* (2018.01)

(52) U.S. Cl.
    CPC .......... *A61B 5/6803* (2013.01); *A61B 5/7271* (2013.01); *A61B 5/7275* (2013.01); *A61B 5/742* (2013.01); *G16H 40/63* (2018.01); *G16H 50/30* (2018.01); *A61B 5/6814* (2013.01); *G16H 50/50* (2018.01)

(56) References Cited

U.S. PATENT DOCUMENTS

| | | | |
|---|---|---|---|
| 2014/0235988 A1* | 8/2014 | Ghosh | A61B 5/7246 600/374 |
| 2015/0080753 A1* | 3/2015 | Miyazaki | A61B 5/7246 600/544 |

OTHER PUBLICATIONS

Junko Hara et al.; "Approximating Dipoles from Human EEG Activity: The Effect of Dipole Source Configuration on Dipolarity Using Single Dipole Models"; IEEE Transactions on Biomedical Engineering; vol. 46; No. 2; Feb. 1999; pp. 125-129.

Junko Hara et al.; "Cortical Atrophy in Alzheimer's Disease Unmasks Electrically Silent Sulci and Lowers EEG Dipolarity"; IEEE Transactions on Biomedical Engineering; vol. 46; No. 8; Aug. 1999; pp. 905-910.

\* cited by examiner

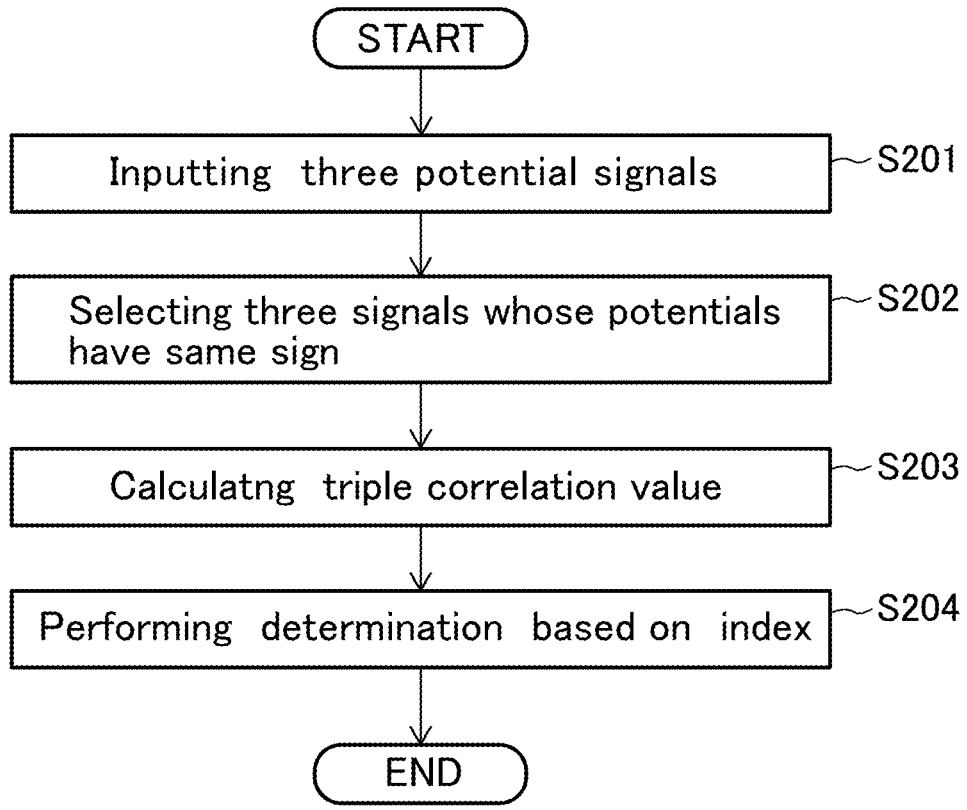
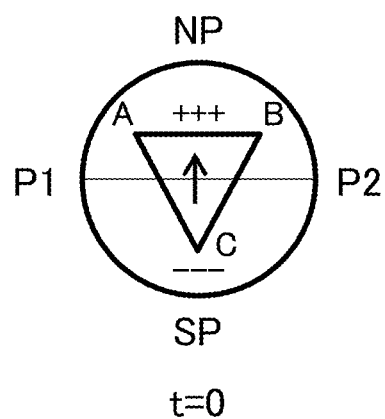

t=T/4 t=T/2 t=3T/4

BRAIN ACTIVITY MEASUREMENT DEVICE, PROGRAM, AND METHOD

TECHNICAL FIELD

The present invention relates to a device, program and method for quantitatively evaluating deterioration in brain function due to a disease such as dementia represented by Alzheimer's disease, by analyzing signals from a deep brain region using a plurality of sensors attached to three different locations on a surface of a head of a subject.

BACKGROUND ART

In Japan, along with aging of the society, over 4 million patients with dementia are imposing increasingly heavy financial and psychological burdens on the entire society. Although there is no medical treatment capable of completely curing dementia so far, early detection of dementia has a potential to slow down progression of dementia by a pharmacological method and appropriate medical care, thereby contributing to significant reduction in health-care cost.

While estimation of an activity in a deep brain region has been conventionally carried out using a PET method, an fMRI method, an MEG method or the like, these methods still involve usability problems and a problem of a need for a large-scale apparatus. In this situation, electroencephalography (EEG) for observing a brain potential (electrical potential) monitored on the scalp (scalp potential) has been widely used in clinical sites because it does not require any large-scale apparatus. In the International 10-20 system used in a standard clinical examination, from a standpoint of, in clinical sites, monitoring a potential distribution on the scalp by a large number of electrodes, potentials have been monitored using 19 electrodes, and recorded in a pen recorder or a hard disk drive in a computer.

As a specific method, there has been developed a system configured to, assuming that a brain potential monitored on the scalp is generated by an equivalent dipole power source assumedly located inside the brain, equivalently express the brain potential by a "dipole tracing method" for inversely estimating a position, direction and current value of the equivalent dipole power source from a brain potential distribution on the scalp (the following Non-patent Document 1). In this system, because both a thalamus acting as part of a source of an α wave and a hypothalamus which is a major part of expression of emotion are located in a brainstem region adjacent to a center of the brain, the technique of assuming an equivalent dipole power source in a deep brain region has been considered to be effective in evaluating activities thereof. As used herein, the term "deep brain region" means a site indicative of a brainstem region and a cerebral limbic system around the brainstem region.

There has also been developed a system (a DIMENSION system) configured to express, by an index, called "dipolarity (Dα)", a degree of accuracy with which the inversely-estimated dipole power source can express a scalp potential. This index is intended to quantitatively analyze a dipole potential activity to estimate an activity of a deep brain region, and largely varies depending on a stage of dementia, so that it has been used as a means to detect dementia (the following Non-Patent Documents 2 and 3).

Further, as a different approach from the above, there has been developed a brain activity measurement device intended to three-dimensionally identify an abnormal site in terms of neuronal activity (the following Patent Document 1).

CITATION LIST

Patent Document

Patent Document 1: JP 5118230 B

Non-Patent Document

Non-patent Document 1: Bin He, Toshimitsu Musha, Yoshiwo Okamoto, Saburo Homma, Yoshio Nakajima and Toshio Sato, "Electric Dipole Tracing in the Brain by Means of the Boundary Element Method and Its Accuracy," IEEE Trans. Biomed. Engnr, Vol. BME-34, No. 6, 406-414, 1987

Non-patent Document 2: J. Hara, T. Musha and W. R. Shankle, Approximating dipoles from human EEG activity: the effect of dipole source configuration on dipolarity using single dipole models, IEEE Trans. Biomed. Eng., 46, 2, 125-129, 1999

Non-patent Document 3: J. Hara, W. R. Shankle and T. Musha, Cortical Atrophy in Alzheimer's Disease Unmasks Electrically Silent Sulci and Lowers EEG Dipolarity, IEEE Trans. Biomed. Eng., Vol. 46, No. 8, 905-910, 1999

SUMMARY OF THE INVENTION

Technical Problem

However, all of the above approaches require a large number of electrodes (generally, 19 electrodes or more) on the scalp, which imposes a heavy burden on a subject. In addition, for quantitatively analyzing the dipole potential activity to estimate the activity of the deep brain region, it is necessary to sort out an α component from a potential appearing in each of the large number of electrodes on the scalp to calculate a degree of approximation of an equivalent dipole potential acquired from the sorted α wave component with respect to the monitored α wave potential, and a standard deviation value indicative of a temporal variation of the approximation degree, thereby leading to a problem of a need for a considerable amount of calculation. Moreover, such a calculation requires electroencephalographic data corresponding to measurement for about 5 minutes, i.e., a relatively long measurement time is required. This also imposes a heavy burden on the subject. There is another problem that reliability of calculation is significantly deteriorated for a subject whose α wave component is weak.

It is therefore an object of the present invention to establish a computing method which is reduced in amount of calculation during evaluation of an activity of a deep brain region, to thereby realize a simplified method using signals acquired from a small number of sensors (electrodes) arranged on a scalp of the subject and capable of reducing the burden on a subject, while quantitatively evaluating deterioration in brain function associated with a disease such as dementia, with a high degree of accuracy.

Solution to Technical Problem

The above technical problems can be solved by the present invention having the following features. Specifically, according to a first aspect of the present invention, there is provided a brain activity measurement device which comprises: a signal acquisition part configured to acquire a signal from a brain of a subject using three sensors attached to different locations on the surface of the head of the subject, wherein at least one of the sensors is attached to the back of the head of the subject; a data extraction part configured to extract, from each of the three signals acquired from the sensors, a deep-brain potential signal having a specific frequency band arising from an activity of a deep brain region, and acquire data from the extracted deep-brain potential signal with a sampling period; a correlation value calculation part configured to calculate a correlation value indicative of a correlative relationship among the deep-brain potential signals acquired from each respective sensors, based on a phase relationship among three pieces of time-series data each extracted from each of the respective sensors by the data extraction part; and an index value calculation part configured to analyze the deep-brain potential signals from the deep brain region, based on the calculated correlation value, to calculate an index value for determining a brain function.

In one embodiment of the first aspect of the present invention, the correlation value calculation part is configured to calculate the correlation value based on a value derived from adding products acquired by multiplying respective ones of a plurality of pieces of data VA(t) extracted within a given time by data VB(t−τ1) and VC(t−τ2) extracted at two time points which are different, respectively, by arbitrary times τ1 and τ2 each of which is equal to or less than a given value and equal to an integral multiple of the sampling period, where VA(t), VB(t) and VC(t) denote, respectively, the three pieces of time-series data extracted from the respective ones of the three sensors, and where the correlation value calculation part is configured to calculate the correlation value with respect to each of one or more possible combinations of the time τ1 and the time τ2.

In another embodiment of the first aspect of the present invention, the correlation value calculation part of the above brain activity measurement device is configured, only when respective ones of the plurality of pieces of data VA(t) extracted within the given time have the same sign as those of the data VB(t−τ1) and VC(t−τ2) extracted at two time points which differ, respectively, by the arbitrary times τ1 and τ2, to subject them to the multiplication, and calculate the correlation value based on a value derived from adding the resulting products, wherein the correlation value is calculated with respect to only combinations of the time τ1 and the time τ2 in the case where the data VA(T), VB(T−τ1) and VC(T−τ2) at a time point T within the given time have the same sign.

In yet another embodiment of the first aspect of the present invention, the brain activity measurement device of the above brain activity measurement device comprises a display part configured to display a three-dimensional map indicative of the correlation values corresponding to the combinations of the time τ1 and the time τ2, in a three-dimensional coordinate having three axes representing, respectively, the time τ1, the time τ2, and the correlation value.

In still another embodiment of the first aspect of the present invention, the index value calculation part is configured to calculate the index value based on a standard deviation of a group of intervals between adjacent ones of a plurality of areas in each of which the correlation value is calculated, in a direction of one of two coordinate axes representing, respectively, the time τ1 and the time τ2, and a standard deviation of a group of intervals between adjacent ones of the plurality of areas in a direction of the other coordinate axes.

In yet still another embodiment of the first aspect of the present invention, the index value calculation part of the above brain activity measurement device is configured to add all of the correlation values calculated with respect to the data VA(t) extracted within a plurality of the given times each having the same time width, every given time, and calculate the index value based on a standard deviation of a group of the correlation values added in each of the plurality of given times.

In another further embodiment of the first aspect of the present invention, the index value calculation part of the above brain activity measurement device is configured to: add a first index sub-value calculated based on a standard deviation of a group of intervals between adjacent ones of a plurality of areas in each of which the correlation value is calculated, in a direction of one of two coordinate axes representing, respectively, the time τ1 and the time τ2, and a standard deviation of a group of intervals between adjacent ones of the plurality of areas in a direction of the other coordinate axes, and a second index sub-value calculated based on a group of the correlation values which are added in each of a plurality of the given times each having the same time width, after being calculated with respect to the data VA(t) extracted within the plurality of given times, every given time; and calculate the index value by subjecting the first and second index sub-values to weighted addition using a given coefficient.

In yet a further embodiment of the first aspect of the present invention, all of the sensors are attached to the back of the head.

In still a further embodiment of the first aspect of the present invention, the brain activity measurement device comprises two or more of the signal acquisition part.

According to a second aspect of the present invention, there is provided a program for analyzing a signal from a deep brain region using three sensors attached to different locations on the surface of the head of a subject, wherein at least one of the sensors is attached to the back of the head of the subject. The program is configured to cause a computer to execute a procedure comprising the steps of: extracting data from each of the three signals acquired by the sensors with a sampling period; calculating a correlation value indicative of a correlative relationship among the signals acquired from each respective sensors, based on a phase relationship among three pieces of time-series data each extracted from the respective sensors; and analyzing the signals from the deep brain region, based on the calculated correlation value, to calculate an index value for determining a brain function.

According to a third aspect of the present invention, there is provided a method for analyzing a signal from a deep brain region using three sensors attached to different locations on the surface of the head of a subject, wherein at least one of the sensors is attached to the back of the head of the subject. The method comprises the steps of: extracting, from each of the three signals acquired from the sensors, a deep-brain potential signal having a specific frequency band arising from an activity of a deep brain region, and acquiring data from the extracted deep-brain potential signal with a sampling period; calculating a correlation value indicative of a correlative relationship among the deep-brain potential signals acquired from each respective sensors, based on a phase relationship among three pieces of time-series data each extracted from the respective sensors; and analyzing the deep-brain potential signals from the deep brain region, based on the calculated correlation value, to calculate an index value for determining a brain function.

Effect of Invention

In the present invention, a correlation value and an index value are introduced so as to establish a computing method which is reduced in amount of calculation, so that it becomes possible to quantitatively analyze whether an activity of the dipole potential assumedly located in the deep brain region is simple or complex, based on signals acquired from a small number of (three) sensors (electrodes) and evaluate deterioration in brain function associated with a disease such as dementia with a high degree of accuracy. In addition, by establishing the computing method which is reduced in amount of calculation, electroencephalographic data required for analyzing the brain activity is reduced to about one minute, so that it becomes possible to reduce a measurement time. As above, the brain activity can be evaluated within a short measurement time, using a small number of electrodes, so that it becomes possible to reduce burden to a subject. Further, by limiting the number of sensors to three, the mechanical fixing of the sensors to the scalp can be maintained significantly easily and stably in the same manner as setting of a tripod, so that it becomes possible to not only significantly shorten a time required for attachment during a measurement operation but also maintain a stable contact resistance to provide improved reliability of acquired data. This improves data reliability and the computing method employing an index value make it possible to improve reliability of calculation for a subject whose α wave component is weak.

BRIEF DESCRIPTION OF THE DRAWINGS

FIG. 2 is a flowchart depicting a flow of a process in the present invention.

FIG. 3a is a diagram depicting a potential on a surface of a uniform sphere model having a dipole power source in a central region thereof.

DESCRIPTION OF THE EMBODIMENTS

[Outline]

With reference to the drawings, a brain activity measurement device according to the present invention will now be described. The following description will be made with respect to a device configuration and a measurement principle, and then with respect to Examples.

[Device Configuration]

Figure 1A:
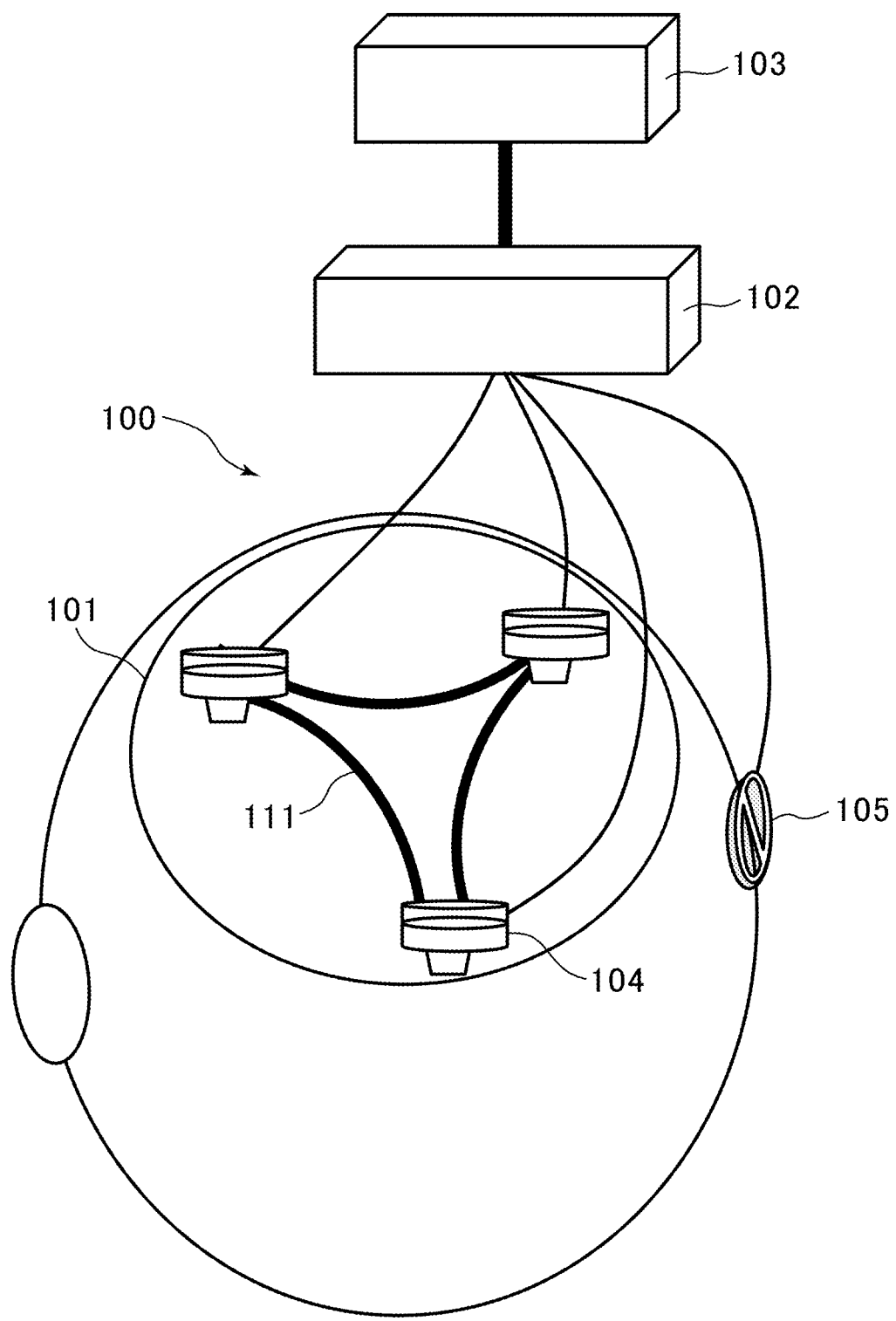
FIG. 1a is a schematic diagram depicting a brain activity measurement device according to one embodiment of the present invention.
Figure 1B:
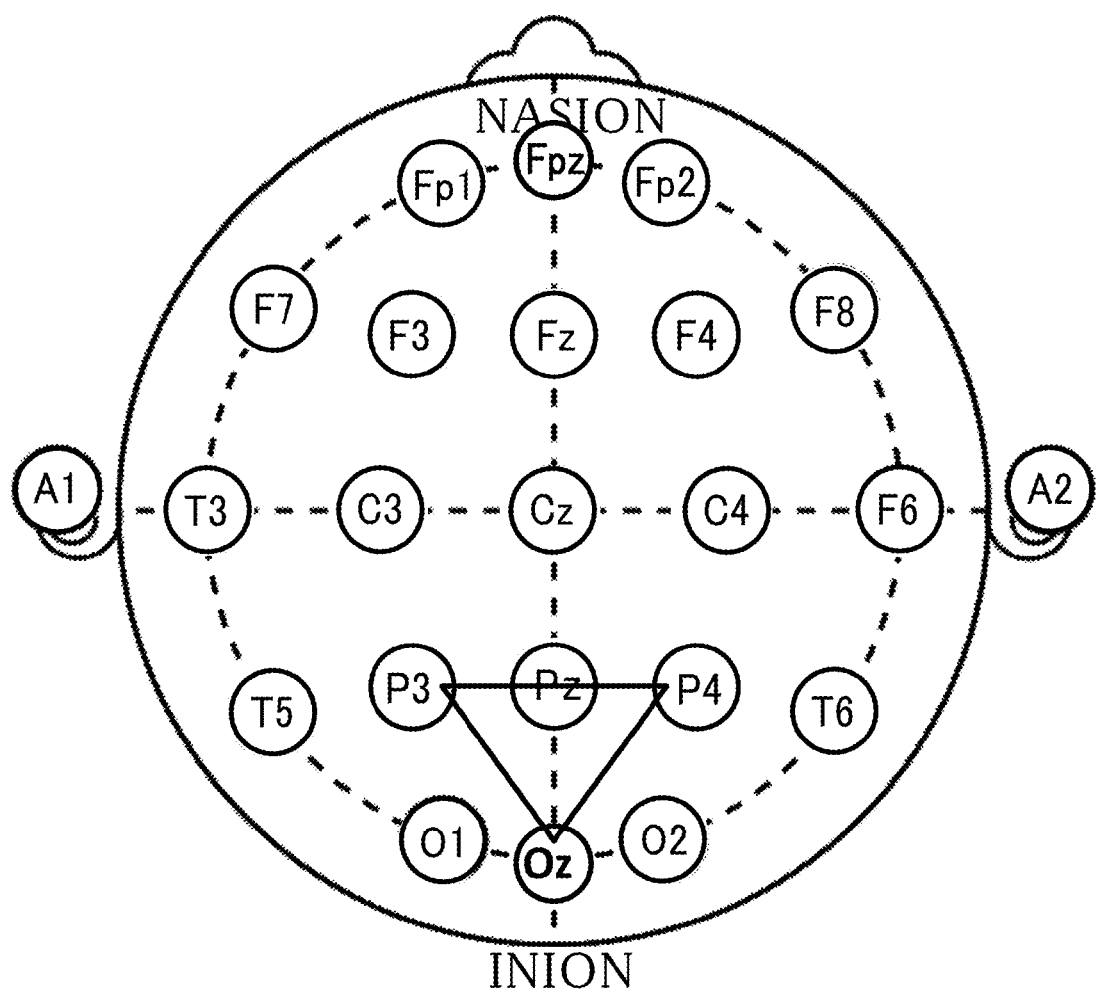
FIG. 1b is a schematic diagram depicting electrode attachment positions in the brain activity measurement device according to this embodiment.

FIGS. 1a and 1b depicts a device configuration of a brain activity measurement device according to one preferred embodiment of the present invention. The brain activity measurement device 100 comprises a head attachment unit 101 equipped with three electrodes 104, a 3-channel amplifier-bandpass filter 102 connected to each of the three electrodes 104 via a signal cable, and an analytical PC 103 connected to the 3-channel amplifier-bandpass filter 102 via a signal cable. The brain activity measurement device 100 also comprises a reference electrode 105 for measuring a reference potential. The reference electrode 105 is used as an indifferent electrode, and is preferably a clip electrode connectable to the earlobe. The reference electrode 105 is connected to the 3-channel amplifier-bandpass filter. In the head attachment unit 101, the three electrodes 104 are fixed to a mounting member 111. For example, the mounting member 111 may be composed of a boomerang-shapes plastic mounting member cut out from a helmet. The head attachment unit 101 is attached to a subject such that the electrodes are arranged, respectively, at three positions among twenty-three positions which are a sum of twenty-one positions in the electrode arrangement according to the International 10-20 System as depicted in FIG. 1b and additional two positions Fpz (defined as a midpoint between Fp1 and Fp2), Oz (defined as a midpoint between O1 and O2). In this case, it is preferable to attach the head attachment unit 101 to the subject such that the three electrodes are arranged, respectively, at P3, P4 and Oz in a back of a head of the subject. Alternatively, the head attachment unit 101 may be realized by selectively using three electrodes in a helmet-type electrode assembly based on the International 10-20 System. In this case, it is also preferable to use three electrodes at the positions P3, P4 and Oz. Each of the electrodes 104 is preferably a porous fiber electrode containing a saline solution, and an upper portion of the electrode 104 may be composed of a metal cylinder for connection to a conductive wire.

Figure 1C:
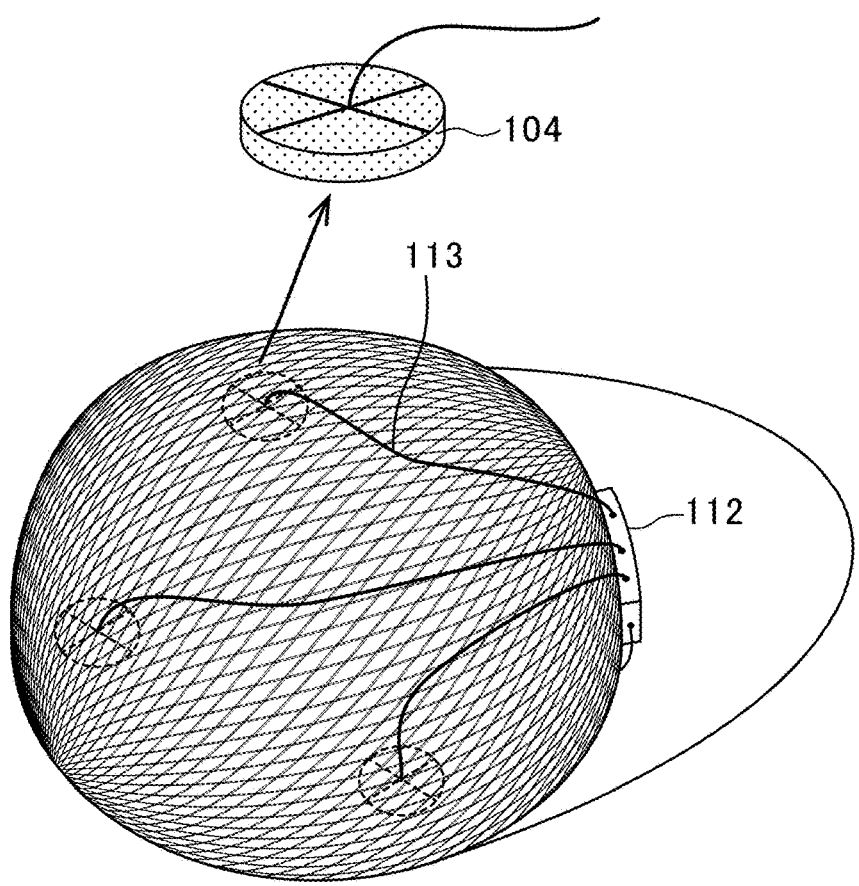
FIG. 1c is a schematic diagram depicting an external appearance of a cap-mounted electrode assembly, in this embodiment.
Figure 1D:
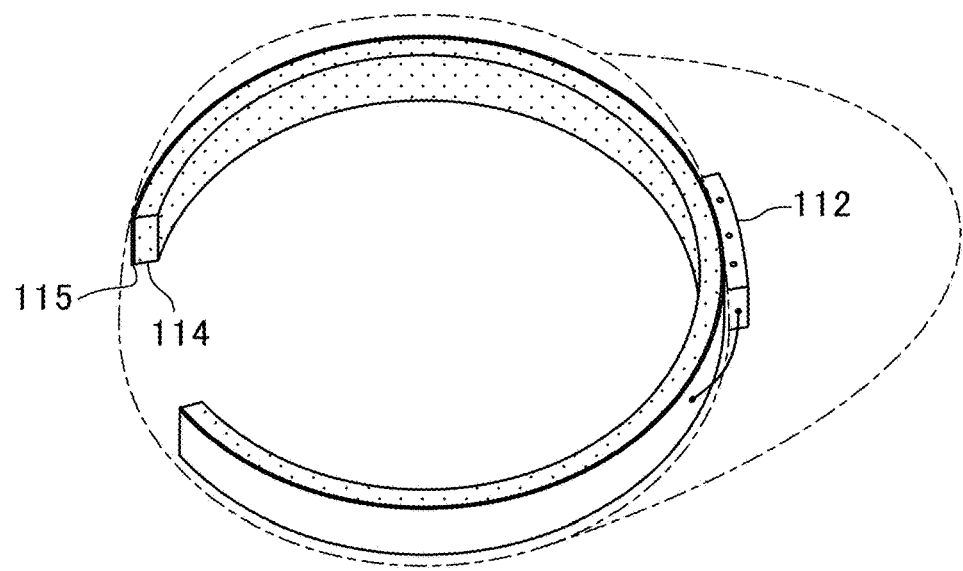
FIG. 1d is a schematic diagram depicting an electroconductive rubber electrode for reference potential measurement, in this embodiment.

As another example, the head attachment unit 101 may be a cap-mounted electrode assembly. FIG. 1c is a schematic diagram depicting an external appearance of the cap-mounted electrode assembly, and FIG. 1d is a schematic diagram depicting an electroconductive rubber electrode serving as the reference electrode 105. The head attachment unit 101 is constructed such that three measurement electrodes 104 are mounted to a mesh-shaped cap. Each of the electrodes 104 is connected to a shielded cable 113 connected to a preamplifier 112, and is preferably formed using porous electroconductive rubber containing a saline solution. The preamplifier 112 has a function of an amplifier in the 3-channel amplifier-bandpass filter 102, and is connected to the analytical PC 103 via a bandpass filter equivalent to that in the 3-channel amplifier-bandpass filter 102. In this example, the reference electrode 105 is constructed as the electroconductive rubber electrode 114 electrically connected to the preamplifier 112, so that the earlobe-connectable clip electrode becomes unnecessary. In this example, in order to achieve potential equalization in the electroconductive rubber and reduction in contact resistance arising from connection of the preamplifier 112 to the cables, a metal film 115 is placed between the arc-shaped electroconductive rubber electrode and the cap.

As yet another example, each of the three measurement electrodes 104 and the reference electrode 105 may be configured to have a wireless communication function, and wirelessly transmit differences between respective ones of three deep-brain potential signals obtained from the (three) measurement electrodes 104 and a brain potential signal obtained from and the reference electrode 105, to the analytical PC 103 which is also configured to have a wireless communication function, as three deep-brain potential signals. Preferably, the reference electrode 105 is disposed at the center of the three measurement electrodes 104. Alternatively, total four signals: three deep-brain potential signals from the measurement electrodes 104; and a brain potential signal from the reference electrode 105, may be transmitted to the analytical PC 103, wherein the analytical PC 103 may operate to calculate differences between respective ones of the three deep-brain potential signals from the measurement electrodes 104 and the brain potential signal from the reference electrode 105, to obtain an input of the three deep-brain potential signals.

As still another example, in place of the electrode 104, it is possible to use a sensor for detecting a change in electricity, magnetism, blood flow or the like. Further, the head attachment unit 101 may comprise two or more sets of the three electrodes. In this case, the activity of the deep brain region may be evaluated more multilaterally.

The analytical PC 103 comprises: a processing unit comprising a CPU and for performing a variety of computations or calculations; a presentation unit (display, printer or the like) for presenting a result of the calculation; a storage unit for storing therein a variety of data and programs; and a communication unit for performing wire/wireless communication. It should be noted that the brain activity measurement device 100 may not comprise the 3-channel amplifier-bandpass filter 102. In this case, the analytical PC 103 may have the function of the bandpass filter 102. Preferably, this function of the bandpass filter, and the parts set forth in the appended claims, such as a data extraction part, a correlation value calculation part, an index value calculation part and a presentation part are realized by executing a given program by the CPU in the processing unit of the analytical PC.

[Measurement Principle]

As described above, the present invention is based on an assumption that the equivalent dipole power source is located in the deep brain region, and the potential distribution measurement for analyzing the dipole potential activity is performed using only three electrodes arranged at different locations on the scalp. Based on the fact that, in the case where a power source is located in the deep brain region, there is a strong phase relationship among respective potential waveforms monitored by the three electrodes, this phase relationship is evaluated. In this way, it is possible to approximately estimate a temporal behavior of the equivalent dipole power source assumedly located in the deep brain region. Taking a seismic wave as an analogy, a seismic wave when a seismic center is located in a surface layer, the seismic wave largely varies in terms of amplitude and phase depending on monitoring points, whereas when the seismic center is located in a deep layer, P waves having approximately the same amplitude and phase are monitored by a plurality of seismometers disposed to be closely spaced apart from each other. The above fact is equivalent to this phenomenon.

Considering that potential waveforms appearing on a surface based on the activity of the deep brain region have substantially the same phase in a plurality of surface areas closely spaced apart from each other, the present invention defines a system of adding only data regarding three potentials having the same sign. That is, data subject to computation is limited to data having the same sign, so that data having a correlation can be extracted. However, it should be noted that the present invention is not limited thereto, but an entirety of data regarding three potentials may be subjected to computation.

In the present invention, as depicted in a flowchart of processing in FIG. 2, upon input of three potential signals (S201), three deep-brain potential signals having the same sign (S202). For example, an earlobe to which a cortical activity is not directly reflected can be used as a detection site for the reference potential for use in determining a sign of potential. In this case, because a DC component is blocked by the amplifier-bandpass filter, whether the sign is positive or negative is determined on a basis of a time average in each of electrodes. Further, it is to be understood that how to acquire the reference potential is not limited thereto, but a electroconductive rubber electrode may also be used. It is also possible to employ a configuration in which differences between respective ones of three deep-brain potential signals obtained, respectively, from the measurement electrodes each having a wireless communication function, and a brain potential signal obtained from a reference electrode disposed at a center of the three electrodes is wirelessly transmitted as three deep-brain potential signal. In this case, the analytical PC 103 functions as a bandpass filter as mentioned above.

Subsequently, a triple correlation value is calculated (S203). On an assumption that low-frequency band potential signals, i.e., deep-brain potential signals, from the three electrodes, are defined, respectively, as EVA(t), EVB(t) and EVC(t), the triple correlation value uses a product of the deep-brain potential signal from one of the three electrodes and the deep-brain potential signals from the remaining two electrodes having time lags $\tau 1$ and $\tau 2$, respectively. The following Formula 1 is one example of a triple correlation value St, where: T denotes a time subject to computation of the triple correlation value; $\Delta t$ denotes a data sampling cycle or period for each of the deep-brain potential signals; and N denotes a constant for normalization and, e.g., the number of times of computation for the product of the three deep-brain potential signals.

$$St = \frac{1}{N} \sum_{t=0}^{T} EVA(t) * EVB(t-\tau 1) * EVC(t-\tau 2)$$
$$= \frac{1}{N} \sum_{t=0}^{T/\Delta t} EVA\left(\frac{\Delta t}{T} \cdot t\right) * EVB\left(\frac{\Delta t}{T} \cdot t - \tau 1\right) *$$
$$EVC\left(\frac{\Delta t}{T} \cdot t - \tau 2\right)$$

Formula 1

An index is calculated by performing a given computation by the analytical PC using the calculated triple correlation value, and identification and determination for a patient with dementia or the like is performed using the calculated index (S204).

A relationship between the triple correlation obtained by the above computation and plotted on a delay parameter space and a behavior of the equivalent dipole power source in the deep brain region will be described using a sphere model formed of a uniform medium. In the following description, for the sake of illustration, portions of the sphere model will be assimilated to the earth, and referred to as North Pole (NP), South Pole (SP), equator or the like.

Figure 3B:
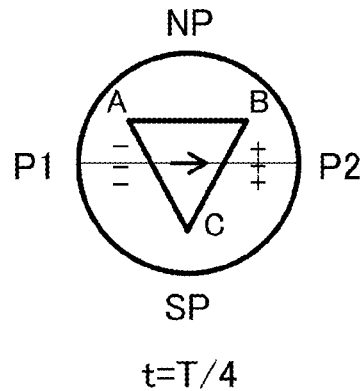
FIG. 3b is a diagram depicting a potential on the surface of the uniform sphere model having a dipole power source in the central region thereof.
Figure 3C:
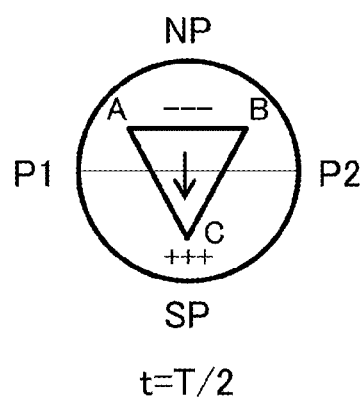
FIG. 3c is a diagram depicting a potential on the surface of the uniform sphere model having a dipole power source in the central region thereof.
Figure 3D:
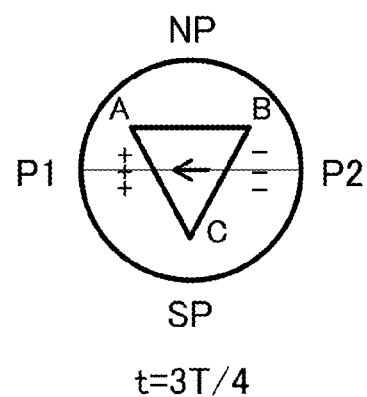
FIG. 3d is a diagram depicting a potential on the surface of the uniform sphere model having a dipole power source in the central region thereof.
Figure 4:
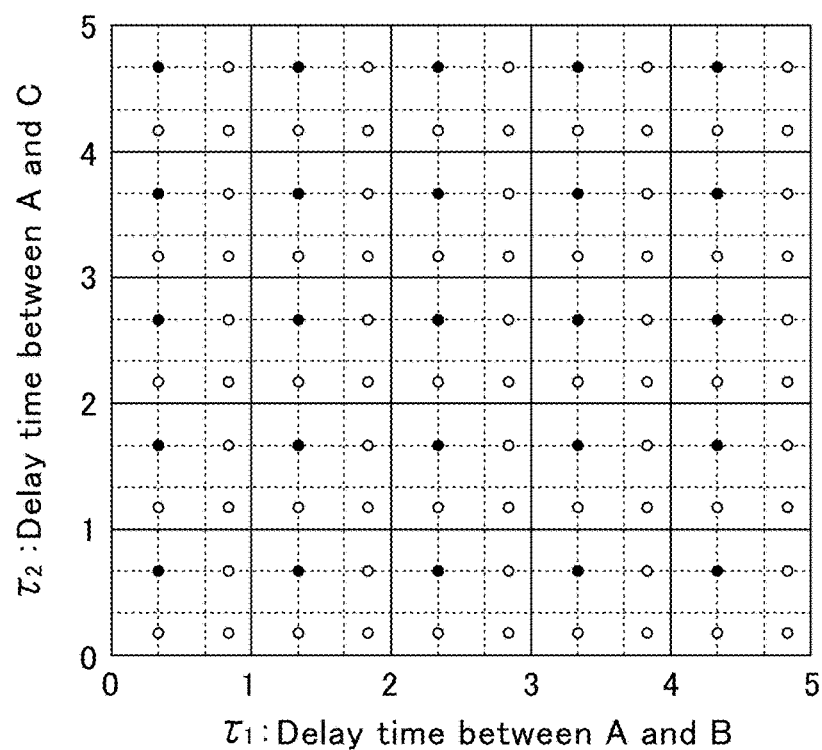
FIG. 4 is a diagram depicting a plot on a delay parameter space.

The activity of the deep brain region is monitored on the surface of the brain in a situation equivalent to that in which there is a minute current source in the deep brain region. Thus, it is assumed that the minute current source is located in a center of the sphere and oriented in a direction from the South Pole toward the North Pole. As depicted in FIG. 3a, a potential distribution formed on a surface of the sphere by the current source has a positive (+) potential in the Northern Hemisphere, a negative (–) potential in the Southern Hemisphere, and a zero potential on the equator. Further, the current source turns in a clockwise direction with a period of T seconds, in a plane including NP, SP, and points P1 and P2 which are different in terms of longitude by 180 degrees on the equator. Every time the current source turns by an angle of 90 degrees, the potential distribution on the sphere surface is sequentially changed, as depicted in FIGS. 3b, 3c and 3d. This potential change is measured by three electrodes A, B and C which are arranged, respectively, at three apexes of an equilateral triangle located on the sphere surface, wherein the triangle is parallel to the plane defined by P1, NP, P2 and SP. The potential waveforms measured from respective ones of the electrodes are used to calculate a correlation value by Formula 1, and a result of the calculation is plotted on a delay parameter space depicted in FIG. 4.

Figure 3E:
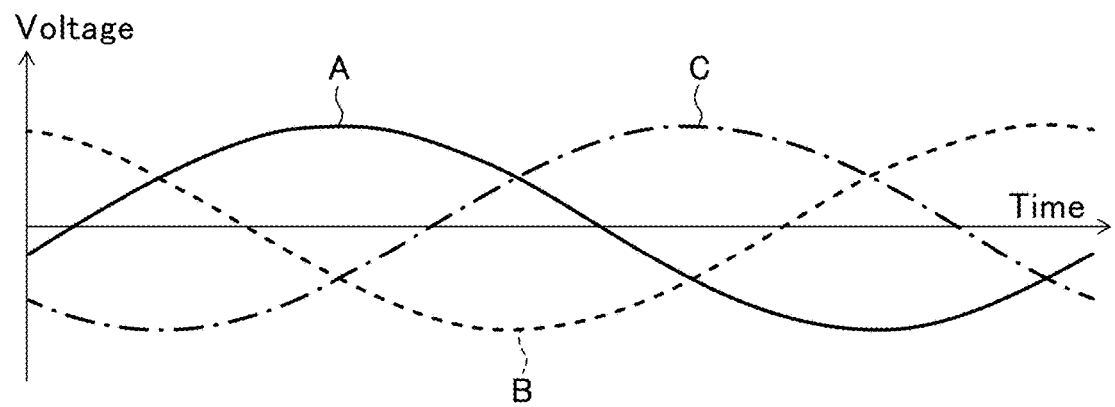
FIG. 3e is a time chart depicting a time evolution of each potential of electrodes A, B and C on the surface of the uniform sphere model having a dipole power source in the central region thereof.

Time evolutions of respective potentials of the electrodes A, B and C are measured as depicted in a graph of FIG. 3e, wherein the potential of each of the electrodes changes in the form of a sinusoidal wave having a period T, with a phase difference of ⅓T with respect to other sinusoidal waves. Reviewing these waves on the basis of the electrode A, values of $\tau 1$ and $\tau 2$ which enable signs of the potentials of the electrodes to become most coincident are ⅓+k and ⅔+k (k: an integer), respectively. Thus, a property having a peak with the period T is obtained as indicated by plots of black circles in vertical and horizontal directions in FIG. 4. Further, at a position (time point) where the potential of one of the electrodes is deviated from each of the peaks by a half period, the potential of one of the electrodes definitely has a phase opposite to those of the potentials of the remaining two electrodes, so that the signs of the potentials of the electrodes never become coincident with each other. Thus, no value is plotted at any position indicated by a plot of a white circle.

As above, the present invention makes it possible to monitor the turning of the equivalent dipole power source in the deep brain region in the form of plots on the two-dimensional delay parameter space, and thus monitor a regular undulation distribution as described later in connection with FIG. 9.

The above description has been made with respect to an example where a single equivalent dipole power source smoothly turns in a spherical deep brain region. On the other hand, in the case where there are a plurality of dipoles or the turning movement is not smooth, plots in individual cases each satisfying the condition requiring coincidence in sign are complicatedly distributed, so that plots in FIG. 4 appear as fine undulation on the delay parameter space as described later in connection with FIG. 10.

EXAMPLE 1

In Example 1, calculation of a triple correlation value for quantitatively evaluating deterioration in brain function due to dementia will be described.

Figure 5:
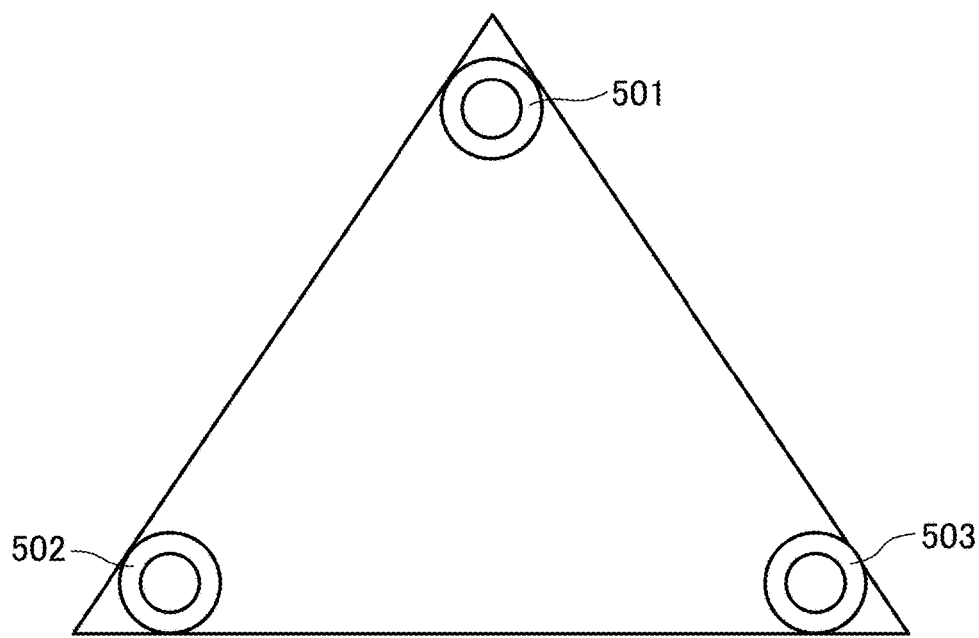
FIG. 5 is a diagram depicting one example of arrangement of measurement electrodes, in Example 1.
Figure 6:
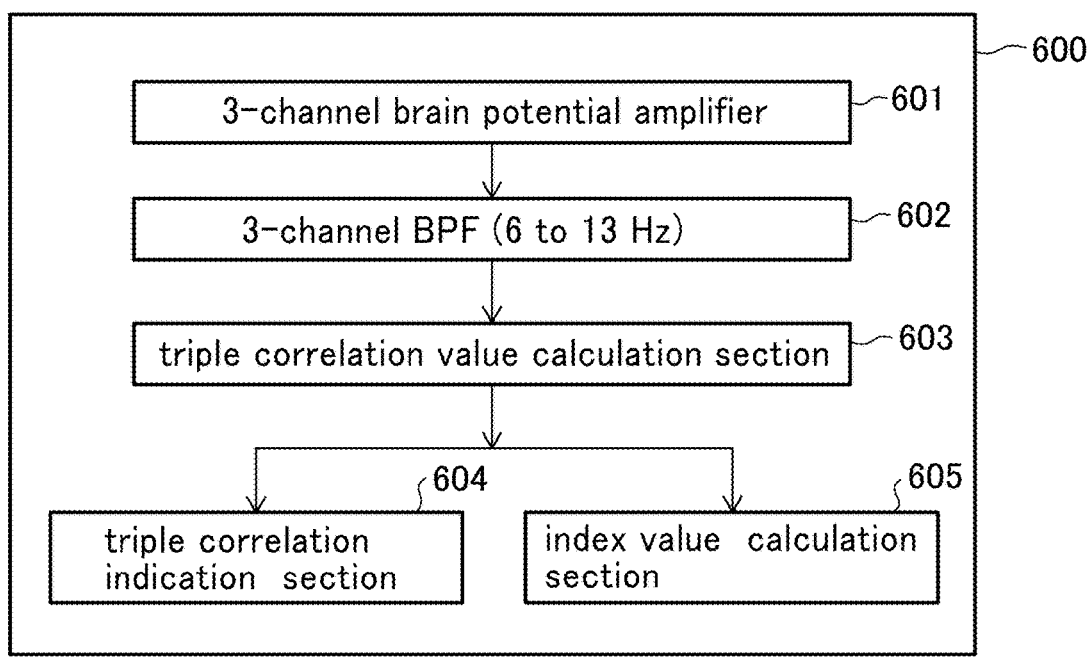
FIG. 6 is a diagram depicting a processing block in a brain potential triple correlation evaluation unit, in Example 1.

As depicted in FIG. 5, three electrodes EA 501A, EB 502, EC 503 are arranged, respectively, at apexes of a triangle, to measure potential signals of VA(t), VB(t), VC(t) as differences between respective ones of the potentials of the electrodes and a potential of a reference electrode disposed separately. Preferably, the electrodes are arranged at positions P3, P4 and Oz, as mentioned above. The potential signals are processed by a triple correlation evaluation unit for deep-brain potential signals. FIG. 6 is a diagram depicting a processing block of a triple correlation evaluation unit 600. For example, this unit is realized by a 3-channel amplifier-bandpass filter and an analytical PC. As depicted in FIG. 6, from three signals amplified by a brain potential amplifier 601, deep-brain potential waveforms each having a specific frequency band primarily consisting of an α waveband, for example, of 6 to 13 Hz are extracted by a bandpass filter 602. This operation is performed to quantitatively analyze an activity of the dipole potential assumedly located in the deep brain region to thereby evaluate an activity of the deep brain region. However, the bandpass filter is capable of detecting specific frequencies primarily consisting of an α wave. Thus, the detectable frequencies are not limited to the values in FIG. 6.

Figure 7:
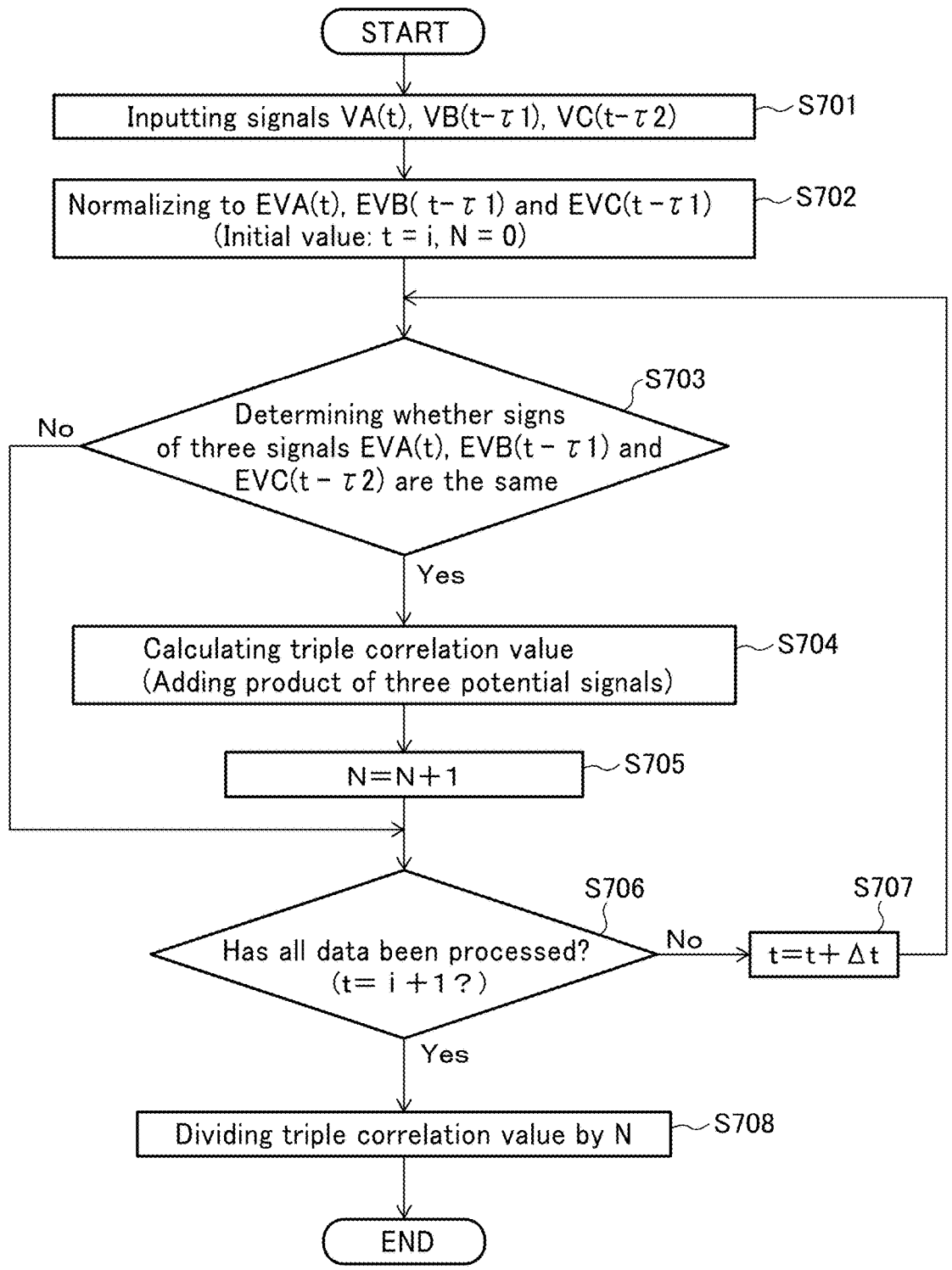
FIG. 7 is a flowchart depicting a flow of a process for calculating a triple correlation value Si in a triple correlation value calculating section, in Example 1.

Next, a method of calculating a triple correlation value S based on the three signals will be described. The extracted signals are processed by a triple correlation value calculation section 603 in a manner as depicted in a flowchart of FIG. 7. FIG. 7 depicts a flowchart of processing for calculating a triple correlation value Si (i=1, 2, . . . , T) within a time period from i sec to i+1 sec. It should be noted that processing performed herein can be modified without departing from the scope and spirit of the present invention.

Upon input of the three signals as mentioned above, data is extracted with a sampling period (S701), and divided, respectively, by standard deviations (σA, σB, σC) calculated with respect to respective potentials of the electrodes, so as to be normalized (S702). This normalization processing is preferably performed, but not limited to, every one second.

$$EVA(t)=VA(t)/\sigma A \quad \text{(Formula 2)}$$

$$EVB(t)=VB(t)/\sigma B \quad \text{(Formula 3)}$$

$$EVC(t)=VC(t)/\sigma C \quad \text{(Formula 4)}$$

The frequency extraction processing by the bandpass filter is performed before or after the normalization processing. Preferably, a noise processing is performed before the normalization processing. For example, the noise processing comprises the steps of 1) removing a segment having +100 μV or more, 2) removing a flat potential (when the potential has a constant value of 25 msec or more), and 3) removing a potential within ±1 μV when it is maintained for 1 second or more.

In this method, assume that, among the above three signals, the signal of the electrode EB and the signal of the electrode EC have, respectively, a time lag of τ1 and a time lag of τ2, with respect to the signal of the electrode E. Then, only when the potentials of all of the three signals have a positive sign (EVA(t)>0, EVB(t)>0, EVC(t)>0), or a negative sign (EVA(t)<0, EVB(t)<0, EVC(t)<0) (S703), the three signals are subjected to processing (S703). As presented in Formula 5, the triple correlation value is derived by adding a product of the three potential signals having time lags (S704). This processing is performed while a sampling point is sequentially shifted by Δt sec until t reaches t=i+1 sec (S706, S707). Further, as is evident from the fact that, in FIG. 7, the triple correlation value Si in the time period from t=i sec to t=i+1 sec is calculated, the triple correlation value Si is not calculated based on all data (T sec) at once, but is derived every given time (in this example, every one second). Then, an average of the resulting T triple correlation sub-values is finally derived as a triple correlation value. The triple correlation value is calculated while each of the time lags τ1, τ2 is also sequentially shifted by Δt sec within one second. For example, assuming that a potential data sampling frequency is defined as fs (Hz), when fs=200 Hz, a product of the three potential signals is calculated while the sampling point is sequentially shifted by Δt=1/fs=0.005 sec. Further, the number of times N signs of the three signals have become positive or negative is derived every one second (S705), and is divided at last (S708), and the triple correlation value is finally divided by N. Formula 5 presents a formula for calculating the triple correlation value Si every one second.

$$S_i(\tau_1, \tau_2) = \frac{1}{N}\int_i^{i+1} |EVA(t) * EVB(t - \tau_1) * EVC(t - \tau_2)| dt \quad \text{(Formula 5)}$$

$$= \frac{1}{N} \sum_{t=(i/\Delta t)}^{(i+1)/\Delta t} EVA(\Delta t \cdot t) * EVB(\Delta t \cdot t - \tau 1) * EVC(\Delta t \cdot t - \tau 2)$$

$$(i = 1, 2, \ldots, T, \tau 1 = \Delta t, 2\Delta t, \ldots, 1(\text{second}), \tau 2 = \Delta t, 2\Delta t, \ldots, 1(\text{second}))$$

In this way, Si is calculated every one second until all data is covered, i.e., t reaches T sec (S1, S2, . . . , ST). Preferably, T (sec) is 10 (sec). However, the calculation method is not limited to calculating Si every one second. Each of the times τ1 and τ2 can take a value which is equal to or less than 1 second and equal to an integral multiple of the sampling period. However, an upper limit of this value is not limited to one second. Further, the sampling period is not limited to 0.005 sec. It should be noted that the triple correlation value can be calculated by Formula 5 without performing the determination about the signs of the three signals.

Figure 8:
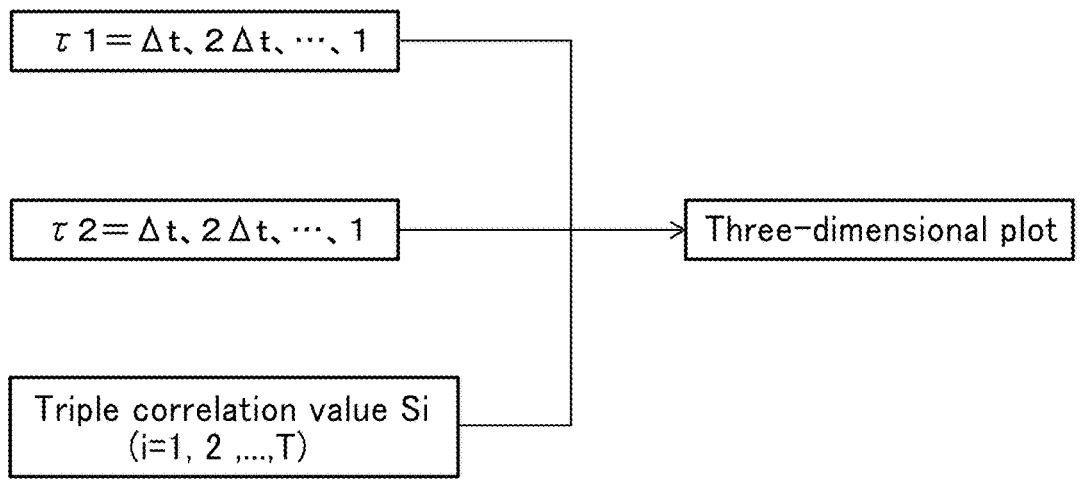
FIG. 8 is a diagram depicting a triple correlation presentation section, in Example 1.

By plotting this result on a feature space formed based on two delay parameters (τ1, τ2) by a triple correlation presentation section 604 as depicted in FIG. 8, it is possible to quasi-three-dimensionally present a triple correlation value distribution plotted on the feature space formed based on the two delay parameters (τ1, τ2). FIG. 9 depicts a quasi-three-dimensional presentation of a triple correlation value distribution in a brain potential waveform of a normal subject, wherein, in order to remove any influence of data having no correlation, only triple correlation values Si (τ1, τ2) obtained under a condition that all of the EVA(t), EVB(t−τ1) and EVC(t−τ2) have the same sign when t is a given value, e.g., t=i+1 are plotted. By limiting the Si to be plotted, in this manner, it is possible to remove noise and quasi-three-dimensionally present the triple correlation value distribution with better accuracy.

Figure 9:
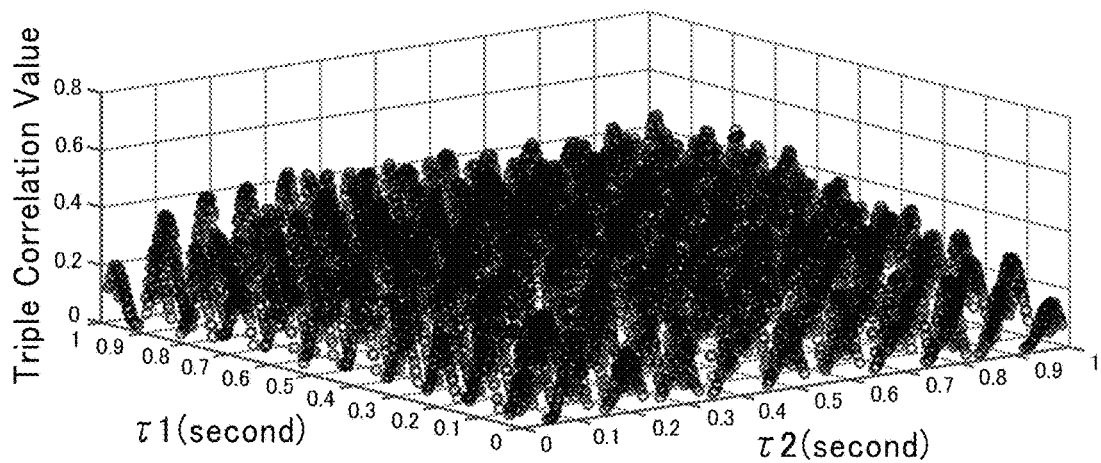
FIG. 9 is a diagram depicting a quasi-three-dimensional presentation of a triple correlation value distribution of a brain potential waveform of a normal subject, in Example 1, wherein the triple correlation value distribution is plotted on a feature space formed by two delay parameters ($\tau 1$, $\tau 2$).
Figure 10:
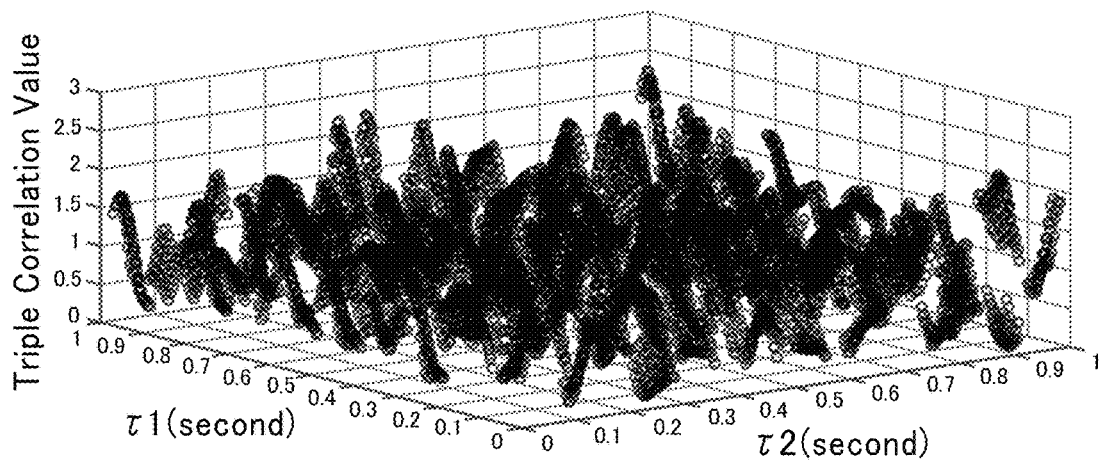
FIG. 10 is a diagram depicting a quasi-three-dimensional presentation of a triple correlation value distribution of a brain potential waveform of a patient with Alzheimer's disease, in Example 1, wherein the triple correlation value distribution is plotted on the feature space formed by the two delay parameters ($\tau 1$, $\tau 2$).

As depicted in FIG. 9, as regards a brain potential waveform monitored from a back of a head of a normal subject, the triple correlation distribution within the feature space is smooth, and moves along with an elapse of monitoring time. For comparison, FIG. 10 depicts a brain potential waveform monitored from a patient with Alzheimer's disease. In the distribution of triple correlation values, small peaks are often distributed complicatedly. In this case, such a distribution also moves along with the elapse of monitoring time. Comparing the two figures with each other, it is proven that a major difference between the triple correlation value distributions of the normal subject and the patient with Alzheimer's disease is in smoothness of the distribution.

EXAMPLE 2

In Example 2, the triple correlation values calculated in Example 1 are used to calculate an index for quantitatively evaluating deterioration in brain function due to dementia.

Figure 11A:
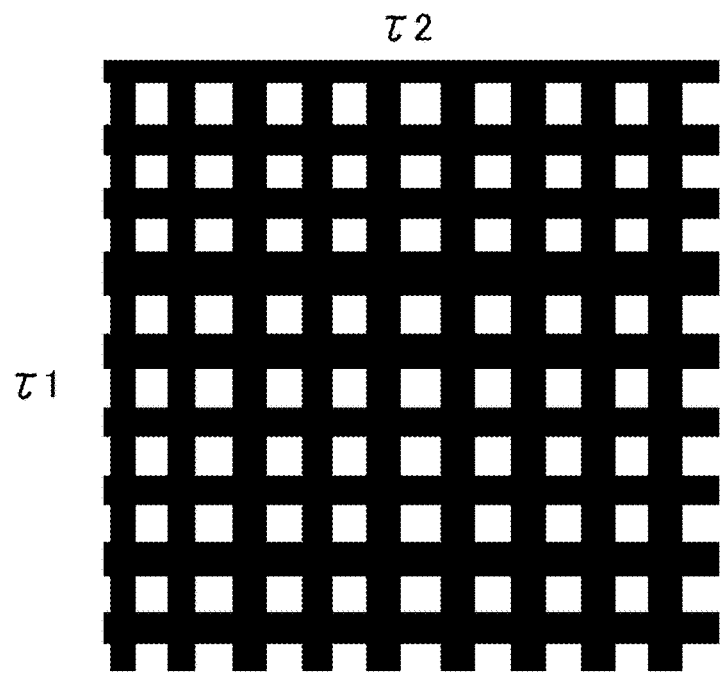
FIG. 11a is a top plan view depicting the three-dimensional presentation for the normal subject in FIG. 9, in Example 2, wherein an area where three deep-brain potential signals have the same positive/negative sign is indicated by white, and an area where any one of the three deep-brain potential signals has a different positive/negative sign is indicated by black.
Figure 11B:
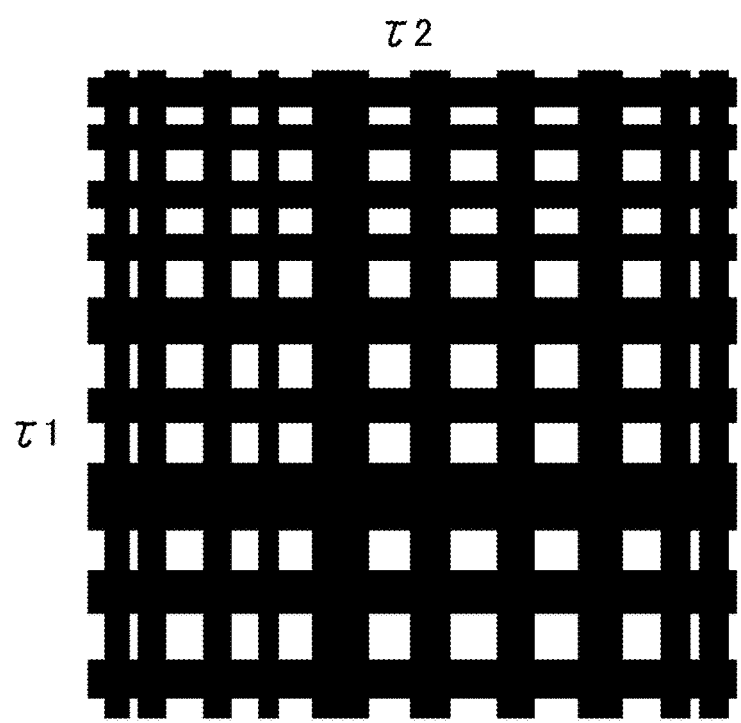
FIG. 11b is a top view depicting the three-dimensional presentation for the patient with Alzheimer's disease in FIG. 10, in Example 2, wherein the area where three deep-brain potential signals have the same positive/negative sign is indicated by white, and the area where any one of the three deep-brain potential signals has a different positive/negative sign is indicated by black.

As described in Example 1, within the two delay time parameter space, data of the normal subject has a forest-like distribution in which tree-like protrusions are regularly arranged side-by-side. On the other hand, in data of the patient with Alzheimer's disease, a forest-like distribution has a large irregularity. In order to quantitatively represent this difference, the coordinate axes are rotated such that lines of trees become parallel to the τ1 axis and the τ2 axis, as depicted in FIG. 11a. FIG. 11a is an example of a normal subject, and is a top view of a three-dimensional presentation depicted in FIG. 10, wherein an area where three waveforms have the same sign is indicated by white, and an area where any one of the three signals has a different sign from those of the remaining signals is indicated by black. As seen in FIG. 11a, when the data is presented in this manner, in the data of the normal subject, a regular checkered pattern is formed, whereas, in the data of the patient with Alzheimer's disease, a checkered pattern become disordered or irregular, as depicted in FIG. 11b. Therefore, in order to quantitatively express this irregularity, the following index is defined.

Figure 11C:
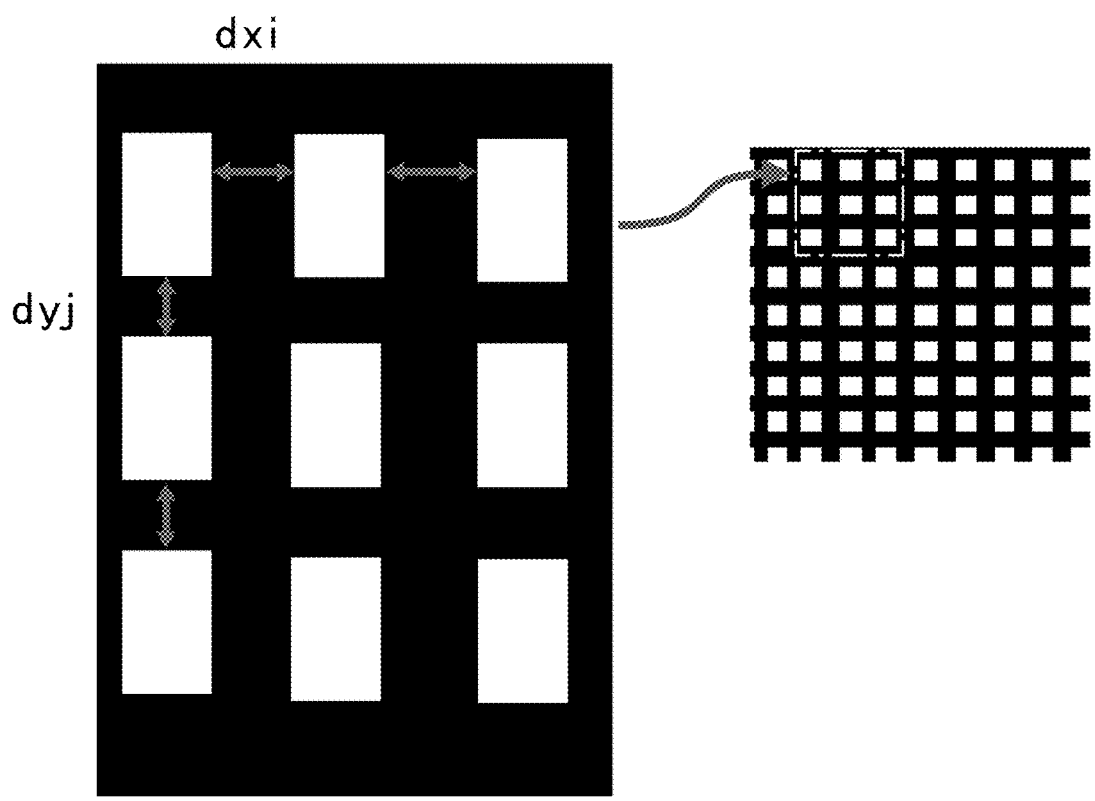
FIG. 11c is an explanatory diagram of each of distances $dx_i$ (i=1, 2, . . . , m), $dy_j$ (j=1, 2, . . . , n) in longitudinal and lateral directions between white rectangular areas during calculation of an index SD in Example 2.

As depicted in FIGS. 11a and 11b, adjacent ones of a plurality of rectangular white areas have a distance or interval therebetween in each of vertical and horizontal directions. Assume that the interval is defined as dxi (i=1, 2, ..., m) and dyj (j=1, 2, ..., n), as depicted in FIG. 11c. By determining whether each of a column of the rectangular white areas and a row of the rectangular white areas are evenly arranged in a corresponding one of the τt direction and the τ2 direction, or arranged irregularly, it is possible to discriminate the normal subject (NL) from the patient with Alzheimer's disease (AD). In AD, a variation in one of the τt and τ2 directions tends to become large. Further, in both of NL and AD, because the white rectangles in each of column and row are regularly arranged, it is possible to perform evaluation based on intervals between adjacent ones of the white rectangles at an arbitrary time in terms of both τ1 and τ2. Specifically, as presented in Formulas 6 and 7, a standard deviations Std_dx of m intervals dxi and a standard deviation Std_dy of n intervals dyj are calculated, and an average of the two standard deviations are determined as an index value SD.

$$\text{std\_dx} = \sqrt{\frac{1}{m}\sum_{i=1}^{m}(dx_i - \overline{dx})^2}, \overline{dx} = \frac{1}{m}\sum_{i=1}^{m}dx_i \quad \text{(Formula 6)}$$

$$\text{std\_dy} = \sqrt{\frac{1}{n}\sum_{j=1}^{n}(dy_j - \overline{dy})^2}, \overline{dy} = \frac{1}{n}\sum_{j=1}^{n}dy_j \quad \text{(Formula 7)}$$

$$SD = |(\text{std\_dx} + \text{std\_dy})/2| \quad \text{(Formula 8)}$$

Figure 12:
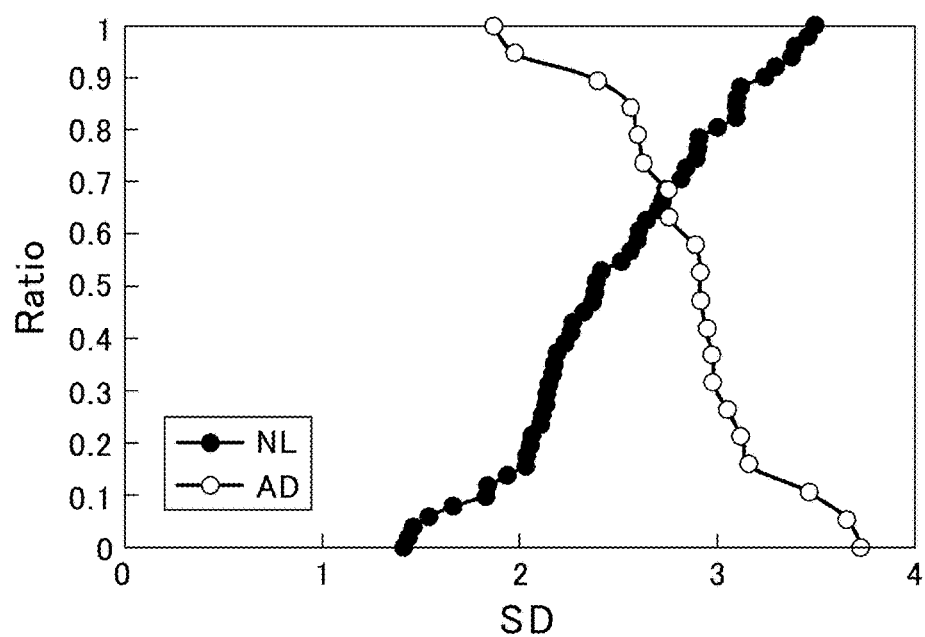
FIG. 12 is a graph depicting sensitivity and specificity curves acquired by using an evaluation index SD in Example 2.
Figure 13:
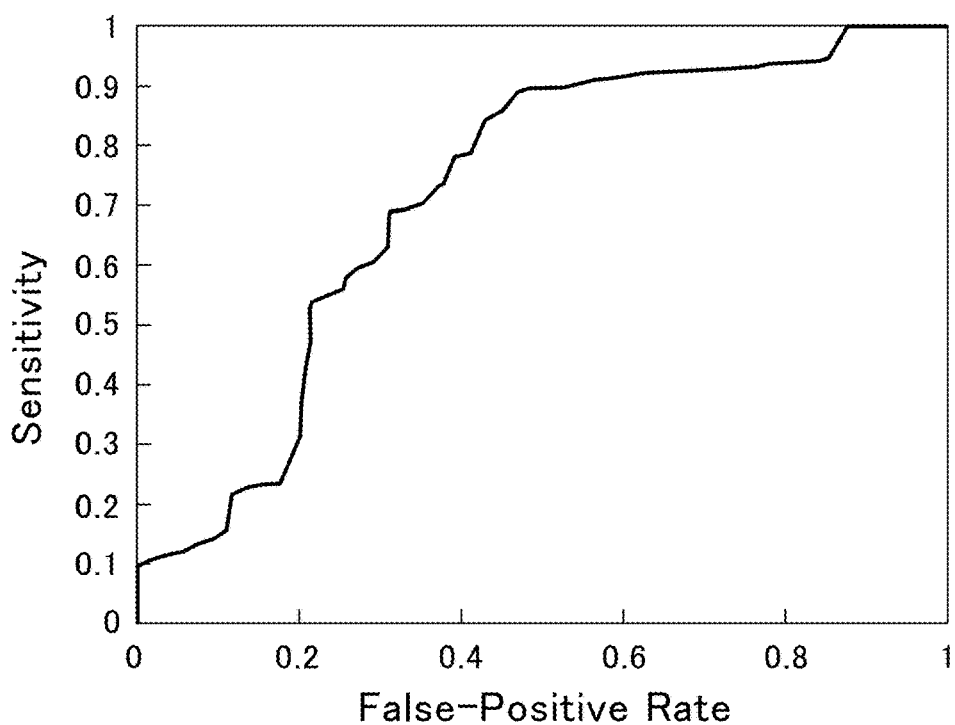
FIG. 13 is a graph depicting a ROC (Receiver Operating Characteristic) curve created from the sensitivity and specificity curves in FIG. 12.

FIG. 12 depicts sensitivity and specificity curves derived from a discrimination result obtained by discriminating 52 examples of normal subjects (NL) and 20 examples of patients with Alzheimer's disease (AD) from each other using the above index SD. As seen in FIG. 12, this index shows an identification rate of 68% at an intersecting point of NL and AD, and it is proven that the index can be used as an effective discrimination index by changing a threshold around the intersecting point. FIG. 13 depicts an ROC curve created from the sensitivity and specificity curves.

The ROC curve represents a relationship between a detection rate and an incorrect diagnosis rate in the case where a detection of Alzheimer's disease is performed. The ROC curve is created from the sensitivity and specificity curves, and used with the sensitivity and specificity curves during a study on how to set a cutoff value between normal and abnormal. In this embodiment, the sensitivity and the specificity indicate, respectively, the patient with Alzheimer's disease and the normal subject, and the false-positive rate is represented by "1-specificity". As one example, creation of the sensitivity and specificity curves and the ROC curve will be briefly described below.

Assume that there are N patients with Alzheimer's disease and M normal subjects. First of all, (i) index values of the patients with Alzheimer's disease and the normal subjects are calculated (N+M index values are calculated). (ii) The index values of the patients with Alzheimer's disease are sorted in descending order, and the index values of the normal subjects are sorted in ascending order. (iii) A ratio (=i/(N−1) (i=0, 1, ..., N−1)) on the vertical axis of the sensitivity and specificity curves is determined such that minimum and maximum values of the index value of the patient with Alzheimer's disease become 0 and 1, respectively, and (iv) a ratio (=i/(M−1) (i=0, 1, ..., M−1)) on the vertical axis of the sensitivity and specificity curves is determined such that minimum and maximum values of the index value of the normal subject becomes 0 and 1, respectively. The index values and values of the ratio for each of the patient with Alzheimer's disease and the normal subjects are plotted and connected to thereby complete the sensitivity and specificity curves, and the intersecting point of the curves is defined as the cutoff value. Each of the number of index values and the number of ratios correspond to a number of patients or subjects. Thus, any space between two plots is connected by means of spline interpolation to form a curve. The ROC curve is created using a vertical axis representing the sensitivity (=a rate of patients with Alzheimer's disease), and a horizontal axis representing the false-positive rate (=1−specificity (a rate of normal subjects)).

As depicted in FIG. 13, when the index SD is used, a false-positive rate providing a sensitivity of about 90% is about 50%, i.e., a good ROC property can be obtained.

EXAMPLE 3

In Example 3, the triple correlation values calculated in Example 1 are used to calculate an index for quantitatively evaluating deterioration in brain function due to dementia.

Triple correlation values of patients with Alzheimer's disease largely vary with respect to τ1 and τ2, as compared to normal subjects. Further, in terms of the triple correlation values per one second calculated by Formula 5 in Example 1, variation in the patients with the Alzheimer's disease is also larger than that in the normal subjects. Thus, a standard deviation in Formula 5 is defined as std_Si, and ten standard deviations (i=1, 2, ..., 10) are calculate. Then, a standard deviation std_S of the ten standard deviations and an average value ave_S of the ten standard deviations are calculated, and a ratio of the standard deviation and the average value is defined as an index Ss.

$$\text{std\_}S_i = \sqrt{\frac{1}{N}\sum_{j=1}^{N}(S_{ij} - \overline{S}i)^2}, \quad \text{(Formula 9)}$$

$$\overline{S}i = \frac{1}{N}\sum_{j=1}^{N}S_{ij}(\tau_1 - \tau_2)$$

$$\text{std\_}S = \sqrt{\frac{1}{10}\sum_{i=1}^{10}(S_i - \overline{\text{std\_}S_i})^2}, \quad \text{(Formula 10)}$$

$$\overline{\text{std\_}S_i} = \frac{1}{10}\sum_{i=1}^{10}\text{std\_}S_i$$

$$\text{ave\_}S = \overline{\text{std\_}S_i} \quad \text{(Formula 11)}$$

$$Ss = \text{ave\_}S/\text{std\_}S \quad \text{(Formula 12)}$$

Figure 14:
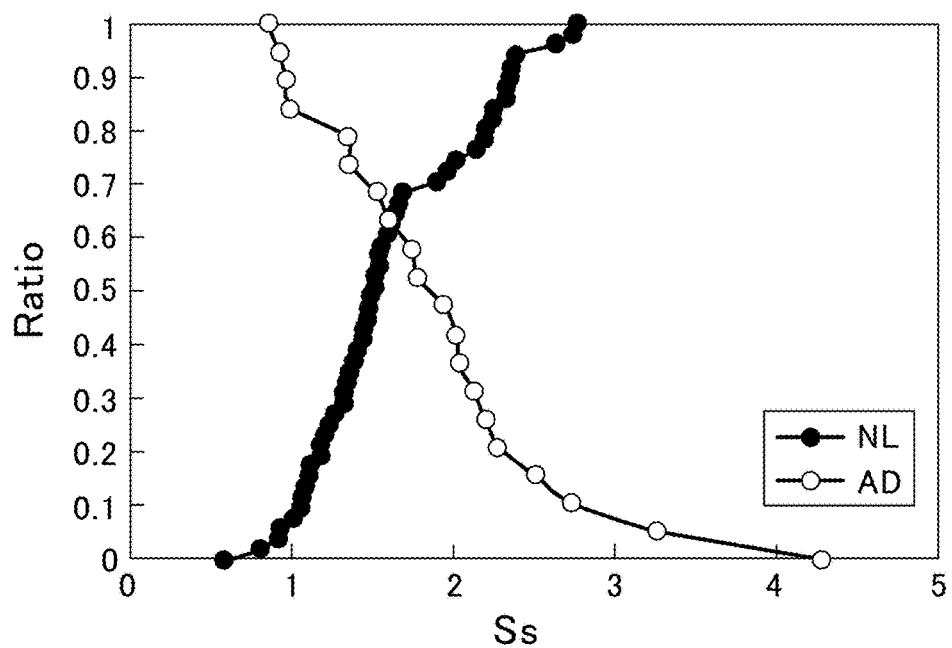
FIG. 14 is a figure showing sensitivity and specificity curves acquired by using an evaluation index Ss in Example 3.

FIG. 14 depicts sensitivity and specificity curves derived from an identification result obtained by discriminating 52 examples of normal subjects and 20 examples of patients with Alzheimer's disease from each other using the above index Ss. As seen in FIG. 14, this index shows an identification rate of 65% at an intersecting point of NL and AD, and it is proven that the index can be used as an effective discrimination index by changing a threshold around the intersecting point.

EXAMPLE 4

In example 4, the index values calculated in Examples 2 and 3 are combined to calculate an index for performing better discrimination.

Figure 15:
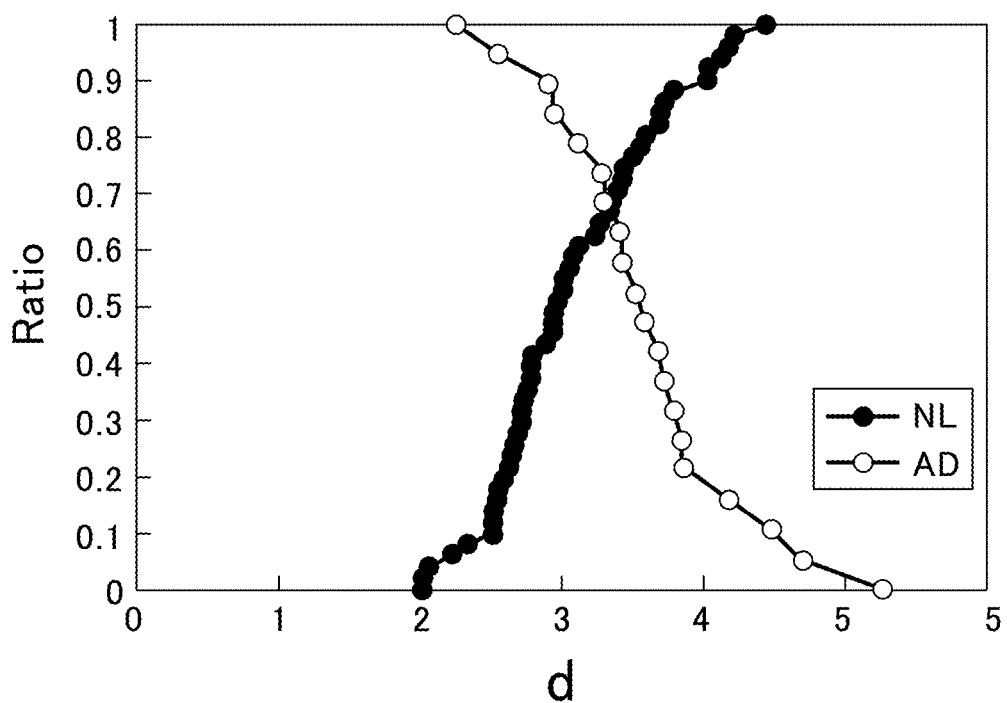
FIG. 15 is a graph depicting sensitivity and specificity curves created when identification of Alzheimer's disease is performed based on an index d (d=0.375×Ss+SD) obtained by linear combination of the indexes obtained in Examples 2 and 3.

FIG. 15 is an example of sensitivity and specificity curves in the case where discrimination is performed based on an index d (d=0.375×Ss+SD) obtained by means of linear combination of the two indices. FIG. 15 shows an identification rate of 70% at an intersecting point of NL and AD. By using the plurality of index values Ss, SD in this manner, it is possible to obtain better discrimination performance. In addition, it is useful in being able to cope with a measurement necessary to be completed within a short period of time. It should be noted that indices and coefficients used in the linear combination are shown by way of an examples, and are not limited thereto.

In addition, by performing a normalization process as described below, it is possible to perform presentation for determining whether a diagnosis result belongs to an AD area or an NL area. Respective average values (Ss_ave, SD_ave) and standard deviations (Ss_std, SD_std) of Ss values and SD values calculated from standard data (20 ADs, 52 NLs) based on the above index d are calculated, and a standardization processing is performed such that such that averages of the Ss values and the SD values become 2 and 2, respectively. The specific calculation formulas are as follows.

$$\text{Ss\_value} = \frac{Ss - \text{Ss\_ave}}{\text{Ss\_std}} * 2 + 2 \quad \text{(Formula 13)}$$

$$\text{SD\_value} = \frac{SD - \text{SD\_ave}}{\text{SD\_std}} * 2 + 2 \quad \text{(Formula 14)}$$

For example, the aforementioned index d can be expressed as the following formula using Ss_value and SD_value in the above formula.

$$d = \text{Ss\_value} * 0.275 + \text{SD\_value} \quad \text{(Formula 15)}$$

Figure 16:
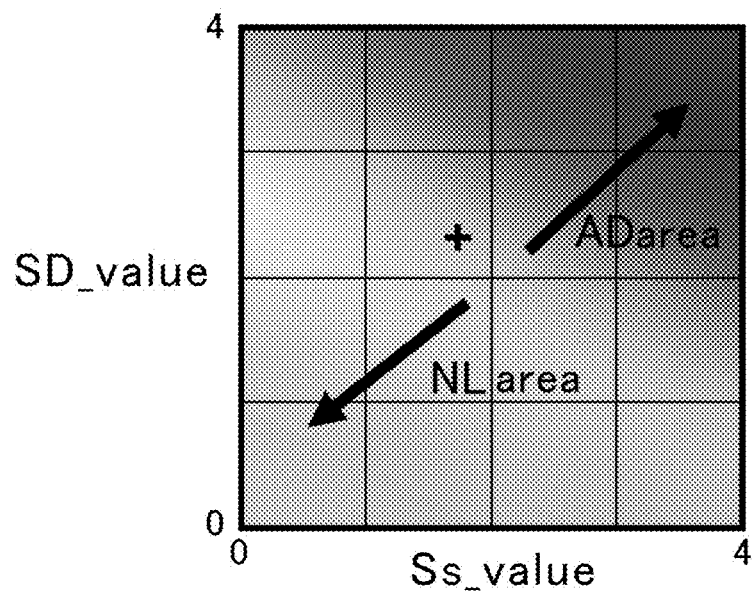
FIG. 16 is a diagram depicting a coordinate presentation for determining whether a diagnosis result is in a NL area or an AD area, based on the indexes obtained in Examples 2 and 3.

By performing such normalization processing and plotting the calculated Ss_value and SD_value on FIG. 16, it is possible to determine whether the diagnosis result belongs to the AD area or the NL area.

Figure 17:
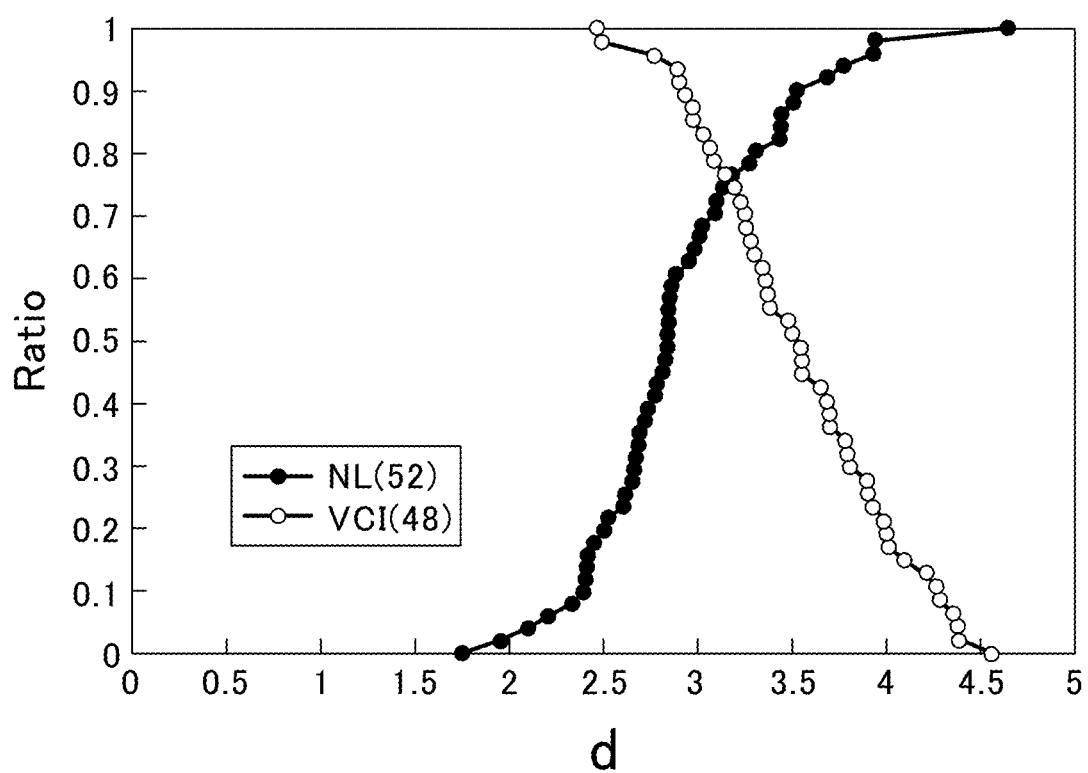
FIG. 17 is a graph depicting sensitivity and specificity curves created when identification of cerebrovascular cognitive impairment is performed based on an index d (d=0.375×Ss+SD) obtained by linear combination of the indexes obtained in Examples 2 and 3.

As another example, FIG. 17 is a graph presenting sensitivity and specificity curves in the case where discrimination of cerebrovascular cognitive impairment is performed based on the index d. A discrimination rate of about 80% is shown at the intersecting point. Thus, it is understood that the present invention is also effective in discriminating vascular cognitive impairment (VCI).

In the processing or operation described above, it is possible to freely change the processing or operation, as long as any inconsistency in processing or operation, e.g., a situation where, in a certain step, data which should not be yet able to be used is used, occurs. Further, although the above examples have been described by way of examples for explaining the present invention, the present invention is not limited to such examples. The present invention can be implemented in various forms without departing from the scope and spirit of the present invention.

LIST OF REFERENCE SIGNS

100: brain activity measurement device
101: head attachment unit
102: 3-channel amplifier-bandpass filter
103: analytical PC
104: electrode
105: reference electrode
111: mounting member
112: preamplifier
113: shielded cable
114: electroconductive rubber electrode
115: metal film
501: electrode EA
502: electrode EB
503: electrode EC
600: triple correlation evaluation unit
601: 3-channel brain potential amplifier
602: 3-channel bandpass filter
603: triple correlation value calculation section
604: triple correlation presentation section
605: index value calculation section

The invention claimed is:

1. A brain activity measurement device comprising:
a signal acquisitioner configured to acquire three signals from a brain of a subject, the signal acquisitioner comprising three sensors configured to be attached to different locations on the surface of the head of the subject, at least one of the sensors configured to be attached to the back of the head of the subject;
a data extractor configured to extract, from each of the three signals acquired from the sensors, a deep-brain potential signal having a specific frequency band arising from an activity of a deep brain region, and acquire data from the extracted deep-brain potential signals with a sampling period;
a correlation value calculator configured to calculate correlation values indicative of a correlative relationship among the deep-brain potential signals acquired from the sensors, based on a phase relationship among three pieces of time series data each extracted from a respective sensor by the data extractor; and an index value calculator configured to analyze the deep-brain potential signals from the deep brain region, based on the calculated correlation values, to calculate index values for determining a brain function.

2. The brain activity measurement device as recited in claim 1, wherein the correlation value calculator is configured to calculate the correlation values based on values derived from adding products acquired by multiplying respective pieces of data of a plurality of pieces of data VA(t) extracted within a given time by data VB(t−τ1) and VC(t−τ2) extracted at two time points which differ, respectively, by arbitrary times τ1 and τ2 each of which is equal to or less than a given value and equal to an integral multiple of the sampling period, where VA(t), VB(t) and VC(t) denote, respectively, the three pieces of time series data extracted from the respective sensor of the three sensors, and wherein the correlation value calculator is configured to calculate the correlation values with respect to each of one or more possible combinations of the time τ1 and the time τ2.

3. The brain activity measurement device as recited in claim 2, wherein the correlation value calculator is configured, only when respective pieces of data of the plurality of pieces of data VA(t) extracted within the given time have the same sign as those of the data VB(t−τ1) and VC(t−τ2) extracted at two time points which differ, respectively, by the arbitrary times τ1 and τ2, to subject the respective pieces of data to the multiplication, and calculate the correlation values based on a value derived from adding the resulting products, wherein the correlation values are calculated with respect to only combinations of the time τ1 and the time τ2 in a case where the data VA(T), VB(T−τ1) and VC(T−τ2) at a time point T within the given time have a same sign.

4. The brain activity measurement device as recited in claim 3, wherein the brain activity measurement device comprises a display configured to display a three-dimensional map indicative of the correlation values corresponding to the combinations of the time τ1 and the time τ2, in a three-dimensional coordinate having three axes representing, respectively, the time τ1, the time τ2, and the correlation values.

5. The brain activity measurement device as recited in claim 3, wherein the index values calculator is configured to calculate the index value based on a standard deviation of a group of intervals between adjacent areas of a plurality of areas in each of which the correlation values are calculated, in a direction of one of two coordinate axes representing, respectively, the time τ1 and the time τ2, and a standard deviation of a group of intervals between adjacent areas of the plurality of areas in a direction of the other coordinate axis.

6. The brain activity measurement device as recited in claim 3, wherein the index value calculator is configured to add all of the correlation values calculated with respect to the data VA(t) extracted within a plurality of given times each having the same time width, every given time, and calculate the index values based on a standard deviation of a group of the correlation values added in each of the plurality of given times.

7. The brain activity measurement device as recited in claim 3, wherein the index value calculator is configured to: add a first index sub-value calculated based on a standard deviation of a group of intervals between adjacent areas of a plurality of areas in each of which the correlation values are calculated, in a direction of one of two coordinate axes representing, respectively, the time τ1 and the time τ2, and a standard deviation of a group of intervals between adjacent areas of the plurality of areas in a direction of the other coordinate axis, and a second index sub-value calculated based on a standard deviation of a group of the correlation values which are added in each of a plurality of given times each having a same time width, after being calculated with respect to the data VA(t) extracted within the plurality of given times, every given time; and calculate the index values by subjecting the first and second index sub-values to weighted addition using a given coefficient.

8. The brain activity measurement device as recited in claim 1, wherein the brain activity measurement device comprises two or more of the signal acquisitioner.

9. A program for analyzing a signal from a deep brain region using three sensors configured to be attached to different locations on the surface of the head of a subject, at least one of the sensors being configured to be attached to the back of the head of the subject, the program being embodied on a non-transitory computer readable structure, and configured to cause a computer to execute a procedure comprising the steps of:

extracting data from each of three signals acquired by the sensors with a sampling period;

calculating a correlation value indicative of a correlative relationship among the signals acquired from the sensors, based on a phase relationship among three pieces of time series data each extracted from a respective sensor; and analyzing the signals from the deep brain region, based on the calculated correlation value, to calculate an index value for determining a brain function.

10. A method for analyzing a signal from a deep brain region using three sensors attached to different locations on the surface of the head of a subject, at least one of the sensors being attached to the back of the head of the subject, the method comprising the steps of:

extracting, with a data extractor, from each of three signals acquired from the sensors, a deep-brain potential signal having a specific frequency band arising from an activity of a deep brain region, and acquiring data, with a signal acquisitioner, from the extracted deep-brain potential signals with a sampling period;

calculating, with a correlation value calculator, a correlation value indicative of a correlative relationship among the deep-brain potential signals acquired from the sensors, based on a phase relationship among three pieces of time series data each extracted from a respective sensor; and analyzing, with an index value calculator, the deep-brain potential signals from the deep brain region, based on the calculated correlation value, to calculate an index value for determining a brain function.

\* \* \* \* \*